United States Patent [19]

Wright

[11] 4,171,310

[45] Oct. 16, 1979

[54] N,N'-DICHLOROBICYCLO[2.2.2]OCT-7-ENE-2,3,5,6-TETRACARBOXYLIC-2,3,5,6-DIIMIDE

[75] Inventor: Ian G. Wright, Greenwood, Ind.

[73] Assignee: Eli Lilly and Company, Indianapolis, Ind.

[21] Appl. No.: 861,734

[22] Filed: Dec. 19, 1977

[51] Int. Cl.$^2$ .................. C07D 487/04; C07D 501/10
[52] U.S. Cl. .................................... 260/326 C; 544/18
[58] Field of Search .................................... 260/326 C

[56] References Cited

U.S. PATENT DOCUMENTS

| 3,345,371 | 10/1967 | Paterson | 260/326 C |
| 3,678,071 | 7/1972 | Touval et al. | 260/326 C |

*Primary Examiner*—Mark L. Berch
*Attorney, Agent, or Firm*—William C. Martens, Jr.; Arthur R. Whale

[57] ABSTRACT

N,N'-Dichlorobicyclo[2.2.2]oct-7-ene-2,3,5,6-tetracarboxylic-2,3,5,6-diimide is useful as a reagent in reactions which require a source of positive chlorine.

1 Claim, No Drawings

N,N'-DICHLOROBICYCLO[2.2.2]OCT-7-ENE-2,3,5,6-TETRACARBOXYLIC-2,3,5,6-DIIMIDE

BACKGROUND OF THE INVENTION

N-chloroimides, in general, have long been recognized as reagents useful in reactions requiring a source of positive chlorine. Examples of such reactions are, for example, oxidation of alcohols, sulfides, amines, and imines; chlorination of amines, reactive aromatic systems, carbonyl compounds having α-hydrogens, and the like. Publications which describe such reactions include R. Filler, Chem. Revs. 63, 21 (1963); and R. Stroh, "Methoden der Organischen Chemie" (Houben-Weil), Vol. 5, Part 3, pp. 760–762, 796 et seq., Georg Thieme Verlag, Stuttgart (1962).

Recently, it has been discovered that a penicillin sulfoxide can be converted to the corresponding 3-methylenecepham sulfoxide by the following sequence:

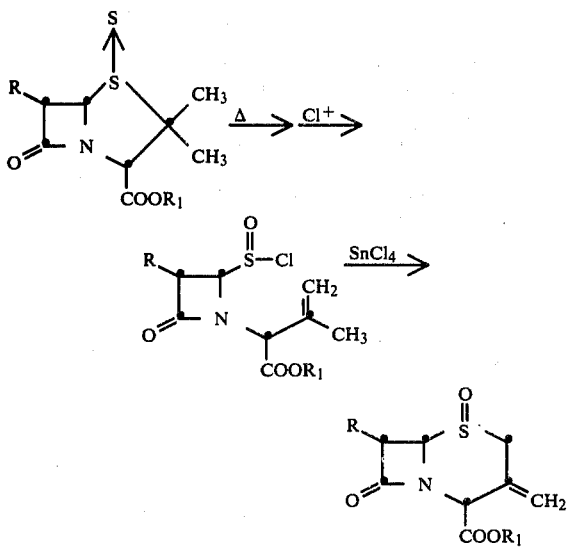

This reaction is reported in Kukolja et al., *Journal of the American Chemical Society*, 98, 5040 (1976) and is further elaborated in Belgian Pat. No. 837,040. From the above it is apparent that the reaction involves a two-step sequence. The first step contemplates thermal generation of the sulfenic acid which then is trapped by oxidation to the sulfinyl chloride. The sulfinyl chloride, in the second step, then, is cyclized to the 3-exomethylenecepham sulfoxide using a Lewis acid reagent, in particular, stannic chloride. The first step, formation of the sulfinyl chloride, requires use of a positive chlorine reagent, and, in particular, an N-chloroimide. Particularly preferred N-chloroimides in accordance with Belgian Pat. No. 837,040 include N-chlorophthalimide, N-chlorosuccinimide, and N-chloroglutarimide.

In carrying out the above penicillin sulfoxide reaction, it is desirable to employ an N-chloroimide having certain properties. First, it is desirable to use an N-chloroimide having a level of reactivity which is neither too great nor to small, that is, a level which provides reaction at readily available conditions while being sufficiently unreactive and stable to provide ease of handling and use in the intended reaction. Secondly, it is desirable to employ an N-chloroimide which will produce, as by product, a corresponding imide which is sufficiently insoluble in the reaction system to permit ready removal from the reaction medium and, thus, easy isolation of the desired product.

These properties are provided by the N-chloroimide of this invention which is N,N'-dichlorobicyclo[2.2.2]-oct-7-ene-2,3,5,6-tetracarboxylic-2,3,5,6-diimide and which has the following structure:

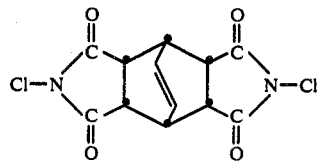

DETAILED DESCRIPTION OF THE INVENTION

As indicated, the compound of this invention is highly suitable for use as a positive chlorine source in the reaction reported by Kukolja et al. since (1) it is both sufficiently stable to permit ready use and sufficiently reactive to provide a ready source of positive chlorine, and (2) it gives rise to a highly insoluble diimide by-product which can be conveniently removed from the reaction medium. The stability of the compound of this invention is indicated by the fact that it melts with decomposition only after being heated to a temperature of 266° C. Furthermore, it remains unaffected after extended periods, for example, 16 hours, of toluene reflux. Other more reactive N-chloroimides are at least partially destroyed by reaction with the solvent when the mixture is maintained for extended periods at elevated temperature. For example, N-chlorosuccinimide is reported to react with toluene (110° C., 16 hours) to produce both ring- and α-substitution. [C. Yavoslavsky and E. Katchalski, *Tetrahedron Letters*, 51, 5173 (1972)].

Moreover, the compound of this invention is sufficiently soluble in organic solvents which are commonly employed in carrying out positive chlorine reactions to permit such reaction to occur. For example, its solubility in boiling toluene is approximately 3 g. per liter. Conversely, its corresponding diimide, the by-product from a positive chlorine reaction, is almost entirely insoluble and thus is readily removable from the reaction mixture. The solubility of the diimide in boiling toluene is less than 25 mg. per liter. Moreover, the diimide by-product is highly stable and crystalline, having a melting point in excess of 410° C.

The compound of this invention can be prepared from the commercially available bicyclo[2.2.2]oct-7-ene-2,3,5,6-tetracarboxylic-2,3,5,6-dianhydride. The dianhydride is treated with ammonia in formamide to produce bicyclo-[2.2.2]-oct-7-ene-2,3,5,6-tetracarboxylic-2,3,5,6-diimide which then is converted to the compound of this invention, for example, by treatment with chlorine in the presence of an epoxy compound and a tertiary amine catalyst.

As indicated hereinbefore, the compound of this invention is a highly useful reagent for carrying out reactions which require a source of positive chlorine.

The following examples are illustrative of the preparation of the compound of this invention.

EXAMPLE 1

Preparation of bicyclo[2.2.2]-oct-7-ene-2,3,5,6-tetracarboxylic-2,3,5,6-diimide.

To 1200 ml. of formamide were added 1007.5 g. (4.06 moles) of bicyclo[2.2.2]-oct-7-ene-2,3,5,6-tetracarboxylic-2,3,5,6-dianhydride. The mixture was heated, and ammonia addition was begun. Ammonia was added as rapidly as the mixture would accept it. An exothermic reaction occurred. The initial temperature of the mixture was 40° C., and, after 7 minutes, the temperature had risen to 140° C. The product began to crystallize. The ammonia addition was discontinued, and distillation of the solvent was begun. After about 1.75 hours, the temperature of the mixture was about 178° C. After 3.75 hours, the temperature of the mixture was 180° C., and 130 ml. of distillate had been collected. Heating was discontinued, and the reaction mixture was allowed to cool under vacuum distillation. After 30 minutes, the temperature of the mixture was 90° C. Vacuum distillation was discontinued, and the reaction mixture was diluted with about 2,000 ml. of acetone. The mixture was cooled in an ice bath to about 5° C. The mixture then was filtered, and the collected product was washed with acetone and dried to give 907.9 (90.8%) of the title compound as a white crystalline solid.

EXAMPLE 2

Preparation of N,N'-dichlorobicyclo[2.2.2]-oct-7-ene-2,3,5,6-tetracarboxylic-2,3,5,6-diimide.

To 1,000 ml. of methylene chloride were added 246.2 g. (1 mole) of bicyclo[2.2.2]-oct-7-ene-2,3,5,6-tetracarboxylic-2,3,5,6-diimide, 600 ml. of propylene oxide, and 4.7 ml. (0.04 mole) of quinoline. The mixture was cooled to 20° C., and chlorine addition was begun at a rate sufficient to permit maintenance of the temperature of the mixture at 20°–30° C. with ice cooling. After about 40 minutes, the mixture began to thicken, and the chlorine addition rate was reduced. After 2.5 hours the chlorine rate was reduced to a slow stream, and the mixture was stirred gently overnight at about 25°–30° C. In the morning, the reaction mixture (25° C.) was white. The rate of chlorine addition was increased, and, after 2.5 hours, the temperature had increased to 30° C. Chlorine addition was discontinued, and the reaction mixture was concentrated in vacuo to remove excess propylene oxide and chlorine. After about 25 minutes, the temperature had decreased to 5° C. The reaction mixture was filtered rapidly, and the filter cake was washed successively with 500–1000 ml. of methylene chloride, ether, toluene, and pentane. The filter cake then was air-dried for several hours, and the solid was further dried in vacuo at 40°–50° C. overnight to obtain 308.4 g. of N,N'-dichlorobicyclo[2.2.2]-oct-7-ene-2,3,5,6-tetracarboxylic-2,3,5,6-diimide. Analysis: Percent Cl+: Theory: 22.5; Found: 21.7. Some methylene chloride may be retained in the product. This is removed by refluxing the N-chloroimide in toluene.

Alternatively, the filter cake recovered from the reaction mixture and containing methylene chloride is transferred directly to a still and toluene is added. The methylene chloride then is removed by fractional distillation. Cooling the toluene to 0°–5° C. and filtering affords almost quantitative recovery of product of higher purity (Percent Cl+: 22.0).

I claim:

1. N,N'-Dichlorobicyclo[2.2.2]-oct-7-ene-2,3,5,6-tetracarboxylic-2,3,5,6-diimide.

* * * * *